US008557775B2

(12) United States Patent
Mine et al.

(10) Patent No.: US 8,557,775 B2
(45) Date of Patent: Oct. 15, 2013

(54) METHOD OF TREATING OXIDATIVE STRESS BY ADMINISTERING COMPOUNDS COMPRISING SERINE-RICH DIPEPTIDES

(76) Inventors: Yoshinori Mine, Aris (CA); Jennifer Kovacs-Nolan, Guelph (CA); Denise Young, North York (CA)

( * ) Notice: Subject to any disclaimer, the term of this patent is extended or adjusted under 35 U.S.C. 154(b) by 0 days.

(21) Appl. No.: 13/377,431

(22) PCT Filed: Jun. 11, 2010

(86) PCT No.: PCT/CA2010/000901
§ 371 (c)(1),
(2), (4) Date: Dec. 19, 2011

(87) PCT Pub. No.: WO2010/142041
PCT Pub. Date: Dec. 16, 2010

(65) Prior Publication Data
US 2012/0087935 A1 Apr. 12, 2012

Related U.S. Application Data

(60) Provisional application No. 61/213,468, filed on Jun. 11, 2009.

(51) Int. Cl.
*A61P 39/06* (2006.01)

(52) U.S. Cl.
USPC ........................................................ 514/15.1

(58) Field of Classification Search
None
See application file for complete search history.

(56) References Cited

U.S. PATENT DOCUMENTS 5,824,315 A 10/1998 Nag
6,184,204 B1 2/2001 Boots et al.

OTHER PUBLICATIONS

Ishikawa S, et al. Biol. Trace Elem. Res. 105(1-3):249-256, 2005.*
Valko, M., et al., Role of oxygen radicals in DNA damage and cancer incidence, Mol.Cell.Biochem., 2004, p. 37-56, vol. 266.
Boveris, A., Chance, B., The Mitochondrial Generation of Hydrogen Peroxide, Biochem.J., 1973, p. 707-716, vol. 134.
Rosen, G.M., et al., Free Radicals and Phagocytic cells, FASEB J., 1995, p. 200, vol. 9.
Powers, S.K., Jackson, M.J., Exercise-Included Oxidative Stress: Cellular Mechanisms and Impact on Muscle Force Production, Physiol.Rev., 2008, 1243-1276, vol. 88.
Aggarwal, B.B., Signalling Pathways of the TNF Superfamily: A Double-Edged Sword, Nat. Rev. Immunology, 2003, 745, vol. 3.
Tak, Paul P. et al, NF-kB: a key role in inflammatory disease, Journal of Clinical Investigation, 2001, 7, vol. 107.
Dalton, T.P., et al., Regulation of Gene Expression by Reactive Oxygen, Annu. Rev. Pharmacol. Toxicology, 1999, p. 67-101, vol. 39.
Morel, Y., Barouki, R., Repression of gene expression by oxidative stress, Biochem. J., 1999, p. 481-496, vol. 342 Pt 3.
Rahman, I., et al., Characterisation of y-glutamylcysteine synthethase-heavy subunit promoter: a critcal role for AP-1, FEBS Lett., 1998, p. 129-133, vol. 427.
Arrigo, Andre-Patrick, Gene Expression and the Thiol Redox State, Free Radical Biology Medicine, 1999, p. 936-944, vol. 27.
Halliwell, B., How to Characterize a Biological Antioxidant, Free Radic. Res. Commun., 1990, p. 1-32, vol. 9:1.
Meister, A,, Anderson M.E., Glutathione, Annu. Rev. Biochem., 1983, p. 711-760, vol. 52.
Griffith, Owen W.,Biologic and Pharmacologic Regulation of Mammalian Glutathione Synthesis, Free Radic. Biol. Med., 1999, p. 922-935, vol. 27.
Myhrstad, M.C., et al., Flavonoids Increase the Intracellular Glutathione level by Transactivation of the y-Glutamylcysteine . . . , Free Radic. Biol. Med., 2002, 386, vol. 32.
Yang, HyeKyung et al, Protective Activities of Stilbene Glycosides from Acer mono Leaves against . . . , J. Agric. Food Chem., 2005, p. 4182-41869, vol. 53.
Brady, D., et al. Inhibition of *Streptococcus* mutans Growth by Hen Egg-delivered Fatty Acids, J.Food Sci., 2003, p. 1433-1437, vol. 68.
Sugita-Konishi, Y. et al, Inhibition of Bacterial Adhesion and Salmonella Infection in BALB/c Mice . . . , J. Agric. Food Chem., 2002, p. 3607-3613, vol. 50.
Katayama, S., et al., Antioxidative stress activity of oligophosphopeptides derived from hen egg yolk . . . , J.Agric. Food Chem., 2006, p. 773-778, vol. 54.
Katayama, S., et al., Oligophosphopeptides derived from egg yolk phosvitin . . . , J. Agric. Food Chem., 2007, p. 2829-2835, vol. 55.
Allerton, S.E., Perlmann, G.E., Chemical Characterization of the Phosphoprotein Phosvitin, J. Biol. Chem., 1965, p. 3892-3898, vol. 240 No. 10.
Kovaks-Nolan. J., et al., Advances in the Value of Eggs and Egg Components for Human Health, J. Agric. Food Chem., 2005, p. 8421-8431, vol. 53.
Jiang, B., Mine Y., Preparation of novel functional oligophosphopetides from hen egg yolk phosvitin, J. Agric. Food Chem., 2000, p. 990-994, vol. 48(4).
Jiang, B., Mine, Y. Phosphopeptides Derived from Hen Egg Yolk Phosvitin: Effect of . . . , Biosci. Biotechnol. Biochem., 2001, p. 1187-1190, vol. 65(5).
Feng, Fengqin, Mine, Y., Phosvitin phosphopeptides increase iron uptake in a Caco-2 cell monolayer model, Int. J. Food Sci. Tech., 2006, p. 455-458, vol. 41.
Merrifield, J., Solid Phase Peptide Synthesis . . . , J. Amer. Chem. Soc., 1963, p. 2149-2154, vol. 85.
Fields, Gregg B. et al, Solid phase peptide synthesis utilizing 9-fluorenylmethoxycarbonyl amino acids, Int. J. Peptide Protein Res., 1990, p. 161-214, vol. 35.
Byrne, Marion B. et al, Amino Acid Sequence of Phosvitin Dervied from the Nucleotide Sequence of Part of the Chicken . . . , Biochemistry, 1984, 4275-4279, 23(19).

* cited by examiner

*Primary Examiner* — Robert Landsman
(74) *Attorney, Agent, or Firm* — Eduardo Krupnik; Miller Thomson LLP

(57) ABSTRACT

The present invention relates to novel serine rich peptides capable of exhibiting antioxidative properties and that can be used to protect a cell, tissues, organs or a multi-cellular organism, such as animals, against oxidative stress. In aspects of the invention, the peptides may be derived from egg yolk proteins utilizing only generally recognized as safe (GRAS) compounds. The invention also relates to cosmetics, functional foods, food supplements or pharmaceutical formulations comprising the peptides of the present invention having antioxidative properties. The cosmetics, functional food or pharmaceutical products are particularly suitable for the care of the skin in protecting against oxidative stress and ageing phenomena.

1 Claim, 7 Drawing Sheets

Glutathione and antioxidative stress enzymes upregulated by both PPP3 (EY) and EYP

METHOD OF TREATING OXIDATIVE STRESS BY ADMINISTERING COMPOUNDS COMPRISING SERINE-RICH DIPEPTIDES

CROSS REFERENCE TO RELATED APPLICATIONS

This application is a national stage application under 35 U.S.C. §371 of International Application No. PCT/CA2010/000901, filed Jun. 11, 2010 which in turn claims the benefit under 35 U.S.C. §119(e) of U.S. Provisional Ser. No. 61/213,468, filed Jun. 11, 2009, the contents of each of which are hereby incorporated by reference into the present disclosure.

REFERENCE TO A "SEQUENCE LISTING," A TABLE, OR A COMPUTER PROGRAM LISTING APPENDIX SUBMITTED ON A COMPACT DISK

A paper copy of the Sequence Listing and a Sequence Listing in computer readable form in .txt format titled "066615_0048Sequencelisting.txt", which was submitted online on Dec. 9, 2011, and is 4.91 KB in size are hereby incorporated by reference. Applicants assert that the paper copy of the Sequence Listing is identical to the Sequence Listing in computer readable form.

FIELD OF THE INVENTION

The present invention relates to compositions and peptide chemistry, more particularly to novel antioxidant peptides, to novel compositions comprising said novel peptides and to methods of obtaining said novel peptides. More particularly yet, the present invention relates to novel antioxidant peptides and compositions comprising said novel peptides, wherein said peptides are derived from egg yolk proteins or are artificially made, and their use as antioxidants.

BACKGROUND OF THE INVENTION

Throughout this application, various references are cited in square brackets to describe more fully the state of the art to which this invention pertains. The disclosure of these references is hereby incorporated by reference into the present disclosure.

Oxidative stress (OS) is a biological state that occurs when a cell's antioxidant capacity is overwhelmed by reactive oxygen species (ROS), causing a redox imbalance. Reactive oxygen species are a type of free radical, which is formed with oxygen. Free radicals are chemical substances that contain one or more unpaired orbital electrons and are therefore unstable and liable to react with other molecules to form more stable compounds with a lower energy state. In an attempt to achieve this stable state, ROS reacts with proteins, lipids, and DNA within the cell. This can result in damage and even inactivation of cellular components such as enzymes, membranes, and DNA. As such, ROS and oxidative stress as a whole have been suggested to participate in the initiation and/or propagation of diseases such as cardiovascular and inflammatory diseases, cancer, and diabetes. [Valko M, et al. Mol. Cell. Biochem. (2004) 266:37]

ROS can be produced on a regular basis during oxidative metabolism and in more potent levels during inflammatory processes. During oxidative metabolism, electrons are lost from the electron transport chain and combine with oxygen, resulting in the formation of superoxide anion (O2—). [Boveris A, Chance B. Biochem. J. (1973)134:707] At the time of inflammation, macrophages and neutrophils that contain the NADPH oxidase complex generate superoxide radicals and hydrogen peroxide to aid in the destruction of foreign agents. [Rosen G M, et al. FASEB J. (1995) 9:200] Environmental factors such as tobacco smoke, UV radiation, exposure to atmospheric oxygen, overexertion during exercise, and the consumption of alcohol and certain foods can also result in the generation of ROS. [Bunker V W. Med. Lab. Sci. (1992) 49:299; Powers S K, Jackson M J. Physiol. Rev. (2008) 88:1243] Though many of these factors can be avoided or limited, as humans, our omnivorous diet exposes us to a variety of foods, some of which may contribute to increased oxidative stress in the gut. An uncontrolled increase of ROS in the gastrointestinal mucosa can lead to inflammatory or ischemic disorders. [Parks D A, et al. Surgery (1983) 94:415; Thomson A, et al. Dig. Dis. (1998) 16:152] Oxidative stress has been postulated to play a role in inflammatory bowel disease (IBD) initiation and progression. The binding of an inflammatory stimulus to its cellular receptor triggers the activation of specific intracellular signaling pathways to upregulate the production of inflammatory mediators. Therefore, antioxidative stress mechanisms and antioxidants are key to limiting the proliferation of ROS and re-establishing a stable redox balance.

ROS, bacterial cell wall lipopolysaccharide (LPS) and the proinflammatory cytokine tumor necrosis factor-alpha (TNF-α) can trigger the activation of multiple signaling pathways including the phosphofylation cascades leading to the activation of mitogen activated protein kinase (MAPKs) and nuclear factor B (NF-κB). [Aggarwal B B. Nat. Rev. Immunol. (2003) 3:745; Tak P P, J. Clin. lnvest. (2001) 107:7] LPS binding to TLR4 and TNF-α to the TNF receptor activate the Ikappa B kinase (IKK)-NF-κB pathway and the three MAPK pathways: ERK 1/2, JNK, and p38. These pathways in turn activate a variety of transcription factors that include NF-κB and activator protein-1 (AP-1). [Dalton T P, et al. Annu. Rev. Pharmacol. Toxicol. (1999) 39:67; Morel Y, Barouki R. Biochem. J. (1999) 342 Pt 3:481] AP-1 binding sites are present in the promotor regions of a large number of proinflammatory cytokine and adhesion molecule genes [Dalton T P, et al. Annu. Rev. Pharmacol. Toxicol. (1999) 39:67; Morel Y, Barouki R. Biochem. J. (1999) 342 Pt 3:481] and play a role in regulating the expression of γ-GCS, the key enzyme in the synthesis of glutathione (GSH). [Rahman I, et al. FEBS Lett. (1998) 427:129] Hydrogen peroxide is able to permeate the cell membrane and act as a cell-signaling molecule by oxidizing the thiol moiety of sulfhydryl-containing proteins involved in signaling transduction pathways [Dalton T P, et al. Annu. Rev. Pharmacol. Toxicol. (1999) 39:67; Morel Y, Barouki R. Biochem. J. (1999) 342 Pt 3:481; Arrigo A P. Free Radic. Biol. Med. (1999) 27:936]. Both NF-κB and AP-1 are redox-sensitive and are both activated during oxidative stress and inflammation. Inhibiting their expression and resulting activity, are key to limiting the expression of oxidative stress and inflammatory mediators.

Aerobic organisms can increase production of biochemical antioxidants such as glutathione (GSH) and induce endogenous antioxidant enzymes like superoxide dismutase (SOD), catalase, thioredoxin reductase (TrxR), glutathione reductase (GR) and glutathione peroxidase (GPx) to inactivate oxidants, forming instead biologically inert products. [Cimino F, et al. Curr. Top. Cell. Regul. (1997) 35:123; Halliwell B. Free Radic. Res. Commun. (1990) 9:1] GSH (γ-glutamylcysteinylglycine) is the major non-enzymatic regulator of redox homeostatis and is ubiquitously present in all cell types. [Meister A, Anderson M E. Annu. Rev. Biochem. (1983) 52:711] It can directly scavenge free radicals or act as a substrate for GPx and glutathione S-transferase (GST) during detoxification of hydrogen peroxide, lipid hydroperoxides and electrophilic compounds. Glutathione is synthesized in two sequential ATP-dependent reactions catalyzed by γ-glutamylcysteine synthetase (γ-GCS) and glutathione synthetase (GS). [Griffith O W. Free Radic. Biol. Med. (1999) 27:922] Recently, food-derived compounds like curcumin and flavonoids have been shown to up-regulate intracellular GSH synthesis. [Biswas S K, et al. Antioxid. Redox Signal (2005) 7:32; Myhrstad M C, et al. Free Radic. Biol. Med. (2002) 32:386] In addition, olive oil biophenols also influence the increase in GPx and GR antioxidant enzyme activities. [Yang HyeKyung, J. Agric. Food Chem. (2005) 53:4182] This demonstrates the role of food-based components in influencing our bodies' intracellular antioxidant defense systems.

A variety of egg components have been cited to possess antimicrobial, antiadhesive, immunomodulatory, anticancer, antihypertensive, and antioxidant activities; behave as protease inhibitors; increase nutrient bioavailability; and provide a source of functional lipids. [Kovacs-Nolan J, et al. J. Agric. Food Chem. (2005) 53:8421] If biologically active properties can be separated into those belonging to the egg white versus the egg yolk, the majority of bioactive peptides thus far have been found in the egg white. This is in part due to the higher percentage composition of egg white (w/v) [Cotterill O J, Geiger G S. Poult. Sci. (1977) 56:1027] and increased variety of egg white proteins compared to that of the yolk. [Sugino H, et al. In: Yamamoto T, Juneja L R, Hatta H, Kim M, editors. Hen Eggs, Their Basic and Applied Science New York: CRC Press; (1997) p. 13].

A variety of egg yolk peptides have been shown to have bioactive qualities. Lipoprotein (LDL) peptides are antimicrobial [Brady D, et al. J. Food Sci. (2003) 68:1433] and sialyiglycopeptides are antiadhesive. [Sugita-Konishi Y, J. Agric. Food Chem. (2002) 50:3607] Phosvitin, an iron-binding highly phosphorylated protein in the egg yolk, was found to have a high affinity for binding calcium, thereby increasing the bioavailability of this nutrient [Jiang B, Mine Y. Biosci. Biotechnol. Biochem. (2001) 65(5)1187] Phosvitin phosphopeptides have also been noted to have antioxidant and more recently, antioxidative stress properties [Katayama S, et al. J. Agric. Food Chem. (2006) 54:773; Katayama S, et al. J. Agric. Food Chem. (2007) 55:2829]

Egg yolk phosvitin is a highly phosphorylated protein with 10% phosphorus monoesterified to 57.5% serine (Ser) residues [Allerton S E, Perlmann G E. J. Biol. Chem. (1965) 240:3892; Taborsky G. Adv. Inorg. Biochem. (1983) 5:235] Oligophosphopeptides (PPPs) prepared from egg yolk phosvitin with 35% phosphate retention, have enhanced calcium- and iron-binding abilities, thereby fulfulling a potential role in increasing their uptake in the intestinal tract. [Jiang B, Mine Y. Biosci. Biotechnol. Biochem. (2001) 65:1187; Jiang B, Mine Y. J. Agric. Food Chem. (2000) 48:990; Feng Feng-Qin, Mine Y. Int. J. Food Sci. Tech. (2006) 41:455] It was previously shown that phosvitin upon alkaline hydrolysis, enzymatic cleavage, and liquid chromatographic separation, resulted in an oligophosphopeptide fraction with antioxidative stress properties. [Katayama S, at al. J. Agric. Food Chem. (2006) 54:773] However, the procedure for obtaining this phosvitin-derived oligophosphopetide fraction utilized non-GRAS (generally recognized as safe) chemicals, was time-consuming and was not "industry-friendly" for scaling up purposes.

It would be desirable, thus, to isolate peptides and compositions capable of inducing an antioxidative response. It would also be desirable to develop a method of preparing and isolating antioxidant peptides and compositions comprising said peptides from a natural source such as egg yolk that use ingredients that are generally recognized as safe (GRAS) for use in food.

The Applicant has now identified novel peptides and compositions capable of inducing an antioxidative response.

SUMMARY OF THE INVENTION

The present invention provides for novel isolated peptides that in aspects are derived from egg yolk and in other aspects are artificially made. The present invention also provides for novel peptides that can be used to protect a cell, tissues, organs or a multi-cellular organism, such as animals, against oxidative stress.

In aspects of the invention, the novel peptides of the invention may be used in vitro, ex vivo or used in vivo as administered to a cell, tissues, organs or multi-cellular organisms such as animals.

Thus, in one aspect, the present invention provides for an isolated peptide characterized in that said isolated peptide comprises an amino acid sequence having a formula X1-(S)n-X2 (SEQ ID NO: 17), wherein X1 is either a blank or is selected from the amino acid residues T, D, A, P, V, K, E and I, X2 is either a blank or is selected from the amino acid residues T, D, A, P, V, K, E and I, "n" is an integer with a minimum value of 2, and "S" is a serine or a phosphoserine residue.

In another aspect of the present invention, the isolated peptide comprises an amino acid sequence selected from the group consisting of SEQ ID NOs: 1 to 16.

In another aspect, the present invention also provides for an isolated DNA fragment and a vector comprising said DNA fragment characterized in that said DNA fragment comprises a nucleotide sequence capable of encoding for a peptide comprising an amino acid sequence of SEQ. ID No. 1 to SEQ ID NO. 14.

In another aspect, the present invention also provides for a peptide capable of inducing an antioxidative response in a cell or in a subject, characterized in that said peptide comprises an amino acid sequence having a formula $X_1$—(S)n-$X_2$ (SEQ ID NO: 17), wherein $X_1$ is either a blank or is selected from the amino acid residues T, D, A, P, V, K, E and I, $X_2$ is either a blank or is selected from the amino acid residues T, D, A, P, V, K, E and I, "n" is an integer with a minimum value of 2, and "S" is a serine or a phosphoserine residue.

In another aspect of the present invention, the peptide capable of inducing an antioxidative response in a cell or in a subject comprises an amino acid sequence selected from the group consisting of SEQ ID NO. 1 to SEQ ID NO. 16, and functional analogues or variants thereof.

In another aspect of the present invention, the peptide capable of inducing an antioxidative response in a cell or in a subject comprises additional serine residues, phosphoserine residues, phosphorous groups or acetyl groups.

In another aspect of the present invention, the peptide capable of inducing an antioxidative response in a cell or in a subject is derived from egg yolk proteins.

In another aspect of the present invention, the peptide capable of inducing an antioxidative response in a cell or in a subject is artificially made.

In another aspect, the present invention also provides for a composition useful in preventing, ameliorating or treating an oxidative reaction in a cell or in a subject, characterized in that said composition comprises one or more of the peptides of the present invention.

In another aspect, the present invention also provides for a composition for maintaining cells, tissues and/or organs in a viable state ex vivo during storage and in vivo during perfusion characterized in that the composition comprises one or more of the peptides capable of inducing an antioxidative response of the present invention.

In another aspect, the present invention also provides for a method for the treatment of an antioxidative stress related disorder or transplantation rejection in a subject, characterized in that said method comprises administering an effective amount of a pharmaceutical composition to said subject, wherein said pharmaceutical composition comprises one or more of the peptides capable of inducing an antioxidative response of the present invention, and a pharmaceutically acceptable carrier.

In another aspect, the present invention also provides for a method for preparing a composition having a mixture of peptides comprising amino acid sequences SEQ ID NOs 1 and 2 characterized in that said method comprises: (a) partially dephosphorylating egg yolk proteins; and (b) enzymatically cleaving the partial dephosphorylated egg yolk proteins thereby obtaining a mixture of egg yolk peptides comprising amino acid sequences SEQ ID NOs 1 and 2.

In aspects of the invention, the partially dephosphorylated egg yolk proteins are cleaved with food grade enzymes which are GRAS (generally recognized as safe).

In another aspect of the present invention, the method for preparing the composition having peptides comprising amino acid sequences SEQ ID NOs 1 and 2 further comprises the following steps: (c) separating the enzymatically cleaved egg yolk proteins into fractions; and (d) selecting the fraction having antioxidative properties.

In another aspect of the present invention, the method for preparing a composition having peptides comprising SEQ ID NOs 1 and 2 is characterized in that said composition further includes peptides comprising SEQ ID NOs 3 to 14, and wherein said method further comprises the following steps: (e) contacting the fraction having antioxidative properties with digestive enzymes, thereby obtaining a digested mixture of egg yolk proteins having antioxidative properties.

In another aspect, the present invention also provides for a method of preparing a composition comprising a mixture of egg yolk peptides having antioxidative properties characterized in that said method comprises: (a) partially dephosphorylating egg yolk proteins; and (b) enzymatically cleaving the partial dephosphorylated egg yolk proteins thereby obtaining the mixture of egg yolk peptides having antioxidative properties.

In another aspect of the present invention, the method for preparing a composition comprising a mixture of egg yolk peptides having antioxidative properties further proteins into fractions; and (d) selecting the fraction having antioxidative properties.

In another aspect of the present invention, the method for preparing a composition comprising a mixture of egg yolk peptides having antioxidative properties further comprises the following steps: (e) contacting the fraction having antioxidative properties with digestive enzymes, thereby obtaining a digested mixture of egg yolk proteins having antioxidative properties.

In another aspect, the present invention also provides for a food or food solution characterized in that said food or food solution comprises one or more of the peptides of the present invention.

In another aspect, the present invention also provides for a nutraceutical composition, characterized in that said nutraceutical composition comprises one or more of the peptides of the present invention.

In another aspect the present invention also provides for a cosmetic composition characterized in that said cosmetic composition comprises one or more of the peptides of the present invention.

Advantages of the invention include:
(1) Peptides and compositions of the invention capable of inducing an antioxidative response that can be obtained from a natural source such as egg yolk.
(2) The compositions of the invention can be manufactured through a procedure that only includes GRAS compounds.
(3) The compositions of the invention can be manufactured through a procedure that is not time consuming and allows for easy scale up.

BRIEF DESCRIPTION OF THE DRAWINGS

The present invention will become more fully understood from the detailed description given herein and from the accompanying drawings, which are given by way of illustration only and do not limit the intended scope of the invention.

DETAILED DESCRIPTION OF THE INVENTION

Figure 1:
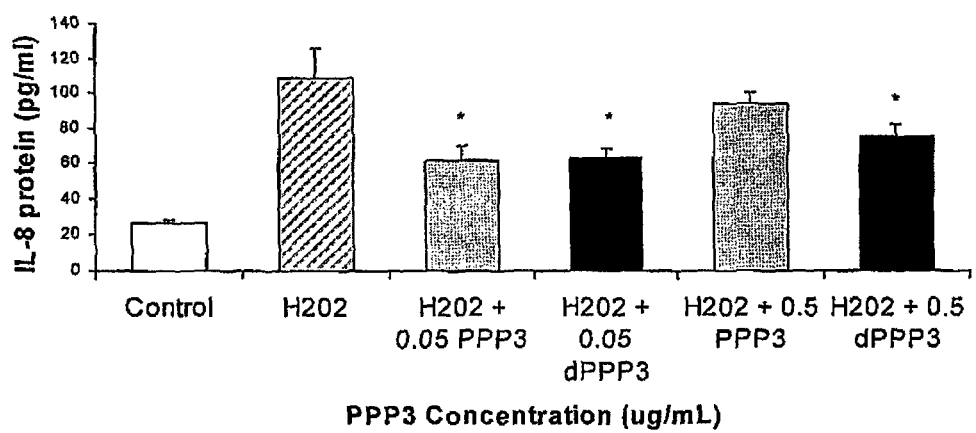
FIG. 1 is a graph representing an analysis of the antioxidative stress activity of digested (dPPP3) and undigested PPP3 (PPP3) egg yolk (EY) fractions comprising the peptides of the instant invention in $H_2O_2$—treated Caco-2 cells. $P<0.05$, compared with cells treated with $H_2O_2$ alone. Data is presented as mean+SD in triplicates.

Unless defined otherwise, all technical and scientific terms used herein have the same meaning as commonly understood by one of ordinary skill in the art to which this invention belongs. Also, unless indicated otherwise, except within the claims, the use of "or" includes "and" and vice-versa. Non-limiting terms are not to be construed as limiting unless expressly stated or the context clearly indicates otherwise (for example "including", "having" and "comprising" typically indicate "including without limitation"). Singular forms included in the claims such as "a", "an" and "the" include the plural reference unless expressly stated otherwise.

The Applicant has identified novel peptides. In aspects of the invention, said peptides are capable of inducing an antioxidative response. Therefore, the present invention has several applications for disorders involving such an etiology.

Taken together, the present invention demonstrates peptides capable of inducing an antioxidative response that in aspects are based on peptides derived from egg yolk and in other aspects based on artificial peptide sequences including at least two consecutive serine residues. The term "peptide" as used herein is defined as a chain of amino acid residues, usually having a defined sequence. As used herein the term peptide is mutually inclusive of the terms "peptides" and "proteins".

According to one aspect, the present invention provides for an isolated peptide characterized in that said peptide comprises an amino acid sequence having a formula: $X_1$—(S)n-$X_2$ (SEQ ID NO: 17), wherein $X_1$ is either a blank (i.e. no residue) or is selected from amino acid residues T (Threonine), D (Aspartic acid), A (Alanine), P (Proline), V (Valine), K (Lysine), E (Glutamic Acid) and I (Isoleucine), $X_2$ is either a blank (i.e. no residue) or is selected from amino acid residues T, D, A, P, V, K, E and I, "n" is an integer $\geq 2$ (i.e. an integer having a minimum value of 2), and "S" is either a serine or a phosphoserine residue.

In one aspect, the isolated peptide of the present invention may include a peptide comprising an amino acid sequence selected from the group consisting of SEQ ID NOs. 1 to 16.

In other aspects the present invention provides for a peptide capable of inducing an antioxidative response, characterized in that said peptide comprises an amino acid sequence having a formula: $X_1$—(S)n-$X_2$ (SEQ ID NO: 17), wherein $X_1$ is either a blank (i.e. no residue) or is selected from amino acid residues T (Threonine), D (Aspartic acid), A (Alanine), P (Proline), V (Valine), K (Lysine), E (Glutamic Acid) and I (Isoleucine), $X_2$ is either a blank (i.e. no residue) or is selected from amino acid residues T, D, A, P, V, K, E and I, "n" is an integer 2 (i.e. an integer having a minimum value of 2), and "S" is either a serine or a phosphoserine residue. In one aspect, a peptide of the present invention capable of inducing an antioxidative response may include a peptide comprising an amino acid sequence selected from the group consisting of: SEQ ID NOs. 1 to 16. In aspects of the invention the peptides capable of inducing an antioxidative response of the present invention comprise an artificial amino acid sequence that includes multiple, consecutive serine or phosphoserine residues. Furthermore, the peptides of the present invention may have cysteines added to one or both ends of the peptides to circularize the peptides by the formation of disulfide bond formation.

The peptides of the invention may be of about at least 2 amino acids in length and about 2 to about 40 amino acids in length and include any ranges of length therein (i.e. 2-35, 2-30, 2-25, 2-20, 2-15, etc.) as is understood by one of skill in the art. Peptides of over about 40 amino acids in length are also encompassed by the present invention. The length of peptide being only restricted by its ability to induce an antioxidative response or to inhibit oxidation. The peptides of the invention may also include dimers and trimers of the peptides as well as additional stabilizing flanking sequences as is understood by those of skill in the art and described for example in U.S. Pat. No. 5,824,315 and U.S. Pat. No. 6,184,204 (the disclosures of which are incorporated herein by reference in their entirety). A multimer according to the invention can either be a homomer, consisting of a multitude of the same peptide, or a heteromer consisting of different peptides. As stated, the amino acid sequences of the peptides according to the invention can be flanked by random amino acid sequences. Preferred are flanking sequences that have a stabilizing effect on the peptides, thus increasing their biological availability. In addition, other peptidomimetics are also useful in the peptides of the present invention. The peptides of the invention also encompass peptides that have been modified by, for example, phosphorylation, glycosylation, lipidation or acetylaton. Furthermore, the peptides of the present invention may also encompass "functionally equivalent to variants" or "analogues" of the peptides. As such, this would include but not be limited to peptides and polypeptides with partial sequence homology, peptides having one or more specific conservative and/or non-conservative amino acid changes and peptide conjugates which do not alter the biological or structural properties of the peptide (i.e. the ability to induce antioxidative stress reaction).

In terms of "functional analogues", it is well understood by those skilled in the art, that inherent in the definition of a biologically functional peptide analogue is the concept that there is a limit to the number of changes that may be made within a defined portion of the molecule and still result in a molecule with an acceptable level of equivalent biological activity, which, in this case, would include the ability to induce an antioxidative reaction. A plurality of distinct peptides/proteins with different substitutions may easily be made and used in accordance with the invention. It is also understood that certain residues are particularly important to the biological or structural properties of a protein or peptide such as residues in the receptor recognition region, such residues of which may not generally be exchanged.

Functional analogues can be generated by conservative or non-conservative amino acid substitutions. Amino acid substitutions are generally based on the relative similarity of the amino acid side-chain substituents, for example, their hydrophobicity, hydrophilicity, charge, size and the like. Thus, within the scope of the invention, conservative amino acid changes means, an amino acid change at a particular position which is of the same type as originally present; i.e. a hydrophobic amino acid exchanged for a hydrophobic amino acid, a basic amino acid for a basic amino acid, etc. Examples of conservative substitutions include the substitution of non-polar (hydrophobic) residues such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another, the substitution of a branched chain amino acid, such as isoleucine, leucine, or valine for another, the substitution of one aromatic amino acid, such as phenylalanine, tyrosine or tryptophan for another. Such amino acid changes result in functional analogues in that they do not significantly alter the overall charge and/or configuration of the peptide. Examples of such conservative changes are well-known to the skilled artisan and are within the scope of the present invention. Conservative substitution also includes the use of a chemically derivatized residue in place of a non-derivatized residue provided that the resulting peptide is a biologically functional equivalent to the peptides of the invention. Therefore, the peptides of the present invention encompass a peptide having an amino acid sequence that differs from SEQ ID Nos. 1-16 and the artificial amino acid sequences by one or more conservative amino acid substitutions. The peptides of the invention also encompass a peptide having an amino acid sequence that differs from SEQ ID Nos. 1-16 as well as the artificial sequences by a single mutation, where the single mutation represents a single amino acid deletion, insertion or substitution.

The peptides of the invention may be further isolated and purified from egg yolk by methods selected on the basis of properties revealed by its sequence. Purification can be achieved by protein purification procedures such as chromatography methods (gel-filtration, ion-exchange and immunoaffinity), by high-performance liquid chromatography (HPLC, RP-HPLC, ion-exchange HPLC, size-exclusion HPLC, high-performance chromatofocusing and hydrophobic interaction chomatography) or by precipitation (immunoprecipitation). Polyacrylamide gel electrophoresis can also be used to isolate the proteins based on the molecular weight of the protein, charge properties and hydrophobicity. The purified proteins can be used in further biochemical analyses to establish secondary and tertiary structure which may aid in the design of pharmaceuticals to interact with the protein, alter the protein charge configuration or charge interaction with other proteins or alter its function.

The peptides of the present invention may be made by methods known to those of skill in the art most notably and preferably by chemical synthesis using techniques well known in the chemistry of proteins such as solid phase synthesis [Merrifield J. Am. Chem. Assoc. (1964) 65:2149; J. Amer. Chem. Soc. (1963) 85:2149; and Int. J. Peptide Protein Res. (1990) 35:161] or synthesis in homogenous solution [Methods of Organic Chemistry, E. Wansch (Ed.) Vol. 15, pts. I and II, Thieme, Stuttgart (1987)] to generate synthetic peptides.

Alternatively, the peptides of the invention may be made by the use of recombinant DNA techniques known to one skilled in the art.

It is further contemplated that the invention encompasses vectors which comprise nucleic acids coding for at least one of the peptides of the present invention.

An aspect of the present invention further encompasses compositions capable of inducing an antioxidative response.

In another aspect, the peptides of the present invention can be used in the manufacture of a composition which may be selected from the group comprising of: food supplements, food solution supplements, nutraceutical compositions, pharmaceutical compositions, milk substitutions, infant formula, total/partial nutritional solutions, storage/reperfusion solutions, cosmetics and pharmaceutical formulations.

The cosmetics, functional food or pharmaceutical products are particularly suitable for the care of the skin in protecting against oxidative stress and ageing phenomena.

According to an embodiment of the invention, a food can include any solid or liquid food product.

According to an embodiment of the invention, a food solution can include but is not limited to soft drinks, milk, juices, and other liquid food products.

According to an embodiment of the invention, a nutraceutical composition is defined as a product that maintains basic physiological, biological, and metabolic functions within an animal, including but not limited to humans.

In aspects, the compositions of the invention comprise one or more of the peptides capable of inducing an antioxidative response for administration to subjects in a biologically compatible form suitable for administration in vivo.

By "biologically compatible form suitable for administration in vivo" is meant a form of the substance to be administered in which any toxic effects are outweighed by the therapeutic effects. Administration of a therapeutically active amount of the pharmaceutical compositions of the present invention, or an "effective amount", is defined as an amount effective at dosages and for periods of time, necessary to achieve the desired result of eliciting an immune response in a human. Suitable administration routes are topical, vaginal, intramuscular injections, subcutaneous injections, intravenous injections, intraperitoneal injections, oral and intranasal administration.

Acceptable carriers are well known to those skilled in the art and include, for example, sterile saline, lactose, sucrose, calcium phosphate, gelatin, dextrin, agar, pectin, peanut oil, olive oil, sesame oil and water.

Furthermore the composition according to the invention may comprise one or more stabilizers such as, for example, carbohydrates including sorbitol, mannitol, starch, sucrose, dextrin and glucose, proteins such as albumin or casein, and buffers like alkaline phosphates. Furthermore, the composition of the present invention may comprise one or more adjuvants that enhance the antioxidant properties of the peptides of the invention.

In one aspect, the present invention provides for a novel composition comprising a mixture of peptides capable of inducing an antioxidative response, wherein said mixture of peptides are derived from egg yolk. The mixture of egg yolk peptides capable of inducing an antioxidative response may be obtained according to the following method:

a) Partially dephosphorylating egg yolk proteins; (b) enzymatically cleaving the partial dephosphorylated egg yolk proteins thereby obtaining the mixture egg yolk peptides.

In aspects of the invention, the partially dephosphorylated egg yolk proteins are cleaved with food grade enzymes which are GRAS (generally recognized as safe). Food grade enzymes which are GRAS include, without limitation, microbial alkalase and protease-m.

As exemplified herein, the Applicant has demonstrated the mixture of egg yolk peptides obtained in step (b) (hereinafter "EYP") is capable of inducing an antioxidative response.

The egg yolk peptides in the EYP mixture capable of inducing an antioxidative response, may be further isolated by (c) separating the enzymatically cleaved egg yolk proteins into fractions; and (d) selecting the fraction having antioxidative properties. The Applicant demonstrated that the EYP fraction having antioxidative properties, referred to as "PPP3 (EY)", includes peptides having an amino acid sequence selected from the group of amino acid sequences set forth in the Sequence Listing as SEQ ID NOs. 1 and 2.

Upon ingestion of protein/peptides, the stomach's pepsin hydrolyses proteins into large oligopeptides, which then get cleaved into short di- or tripeptides and free amino acids by trypsin and chymotrypsin in the small intestine. Given that the peptides in PPP3 (EY) have a large size and negative charge, both digested and undigested PPP3 (EY) may interact with cell surface receptors in the digestive tract and influence intracellular cell signaling in this manner.

Accordingly, the applicant digested PPP3 (EY) with digestive enzymes to simulate the conditions in the digestive system and demonstrated that the digested PPP3 (EY) fraction (dPPP3) retained the antioxidative stress properties of the undigested PPP3 (EY), as illustrated in FIG. 1.

The Applicant has further demonstrated that said dPPP3 (EY) fraction includes peptides having the amino acid sequences set forth in the Sequence Listing as SEQ ID NOs. 3 to 14.

Figure 2:
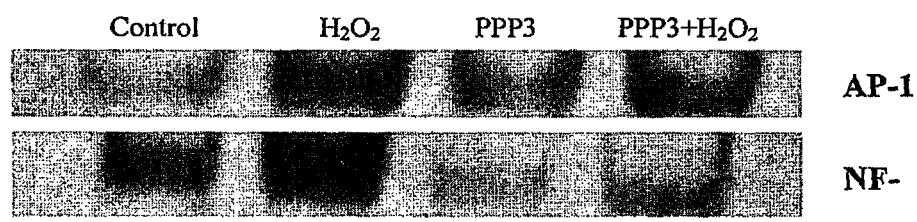
FIG. 2 shows the effect of PP3 (EY) on AP-1 and NF-κB in $H_2O_2$—treated Caco-2 cells.

With reference to FIGS. 1 and 2, using in vitro experiments, the Applicant has demonstrated that Caco-2 cells pre-exposed to the fraction PPP3 (EY) obtained from egg yolk and comprising peptides SEQ ID NO. 1 and 2 prior to the incubation of the cells in $H_2O_2$, were capable of decreasing the cellular concentration of oxidative stress mediators IL-8, NF-κB and AP-1 to levels that were significantly lower than the concentration levels of these mediators in control $H_2O_2$—treated Caco-2 cells that were not pre-treated with PPP3 (EY). FIG. 1 further demonstrates that dPPP3 (EY), which comprises peptides having the amino acid sequences set forth in the Sequence Listing as SEQ ID NOs. 3 to 14, was also capable of protecting Caco-2 cells from oxidative stress.

In aspects of the invention, said digestive enzymes include, without limitation, pepsin, trypsin, chymotrypsin and pancreatin.

Figure 3:
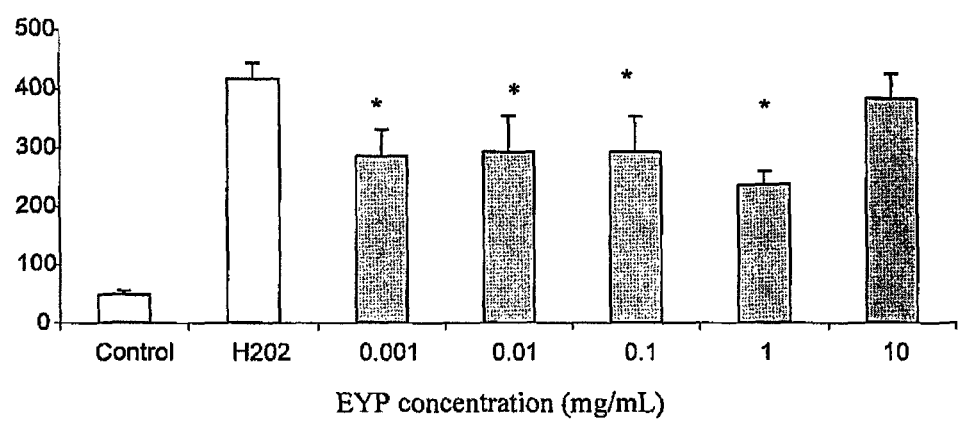
FIG. 3 is a graph illustrating an analysis of the antioxidative stress activity of EYP in $H_2O_2$—treated Caco-2 cells. $*P<0.05$, compared with cells treated with $H_2O_2$ alone. Data is presented as mean+SD in triplicates.

With reference to FIG. 3, using in vitro experiments, the Applicant has further demonstrated that pre-treatment of Caco-2 cells with a composition comprising EYP, prior to the incubation of the Caco-2 cells in $H_2O_2$, resulted in a cellular concentration of oxidative stress mediator IL-8 that was significantly lower than the concentration of IL-8 in control $H_2O_2$—treated Caco-2 cells. Since EYP is reducing IL-8 concentrations to levels similar to those observed with PPP3 (EY) in FIG. 1, the active component in EYP is likely to be PPP3 (EY).

Figure 4:
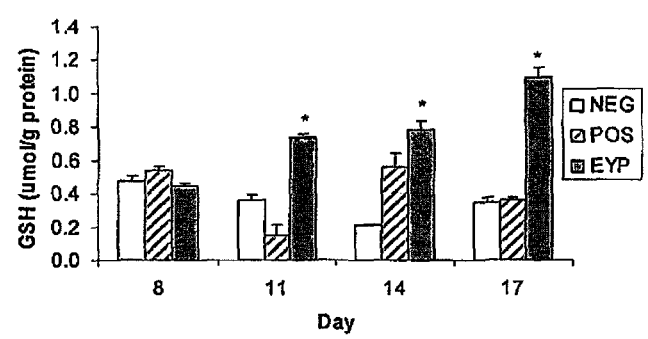
FIG. 4 is a graph illustrating total GSH concentration in red blood cells in pigs over time in 3 experimental groups consisting of negative controls (NEG), positive controls (POS), and egg yolk peptide (EYP). Each bar represents mean+SEM; n=5. $*P<0.05$, compared with positive group.

With reference to FIG. 4, using in vivo experiments, the Applicant demonstrated that upon exposing pigs to $H_2O_2$, the total concentration of glutathione (GSH) over time in the red blood cells is significantly increased when pigs are fed with food supplemented with a composition of the present invention comprising EYP prior to being exposed to $H_2O_2$.

Figure 5:
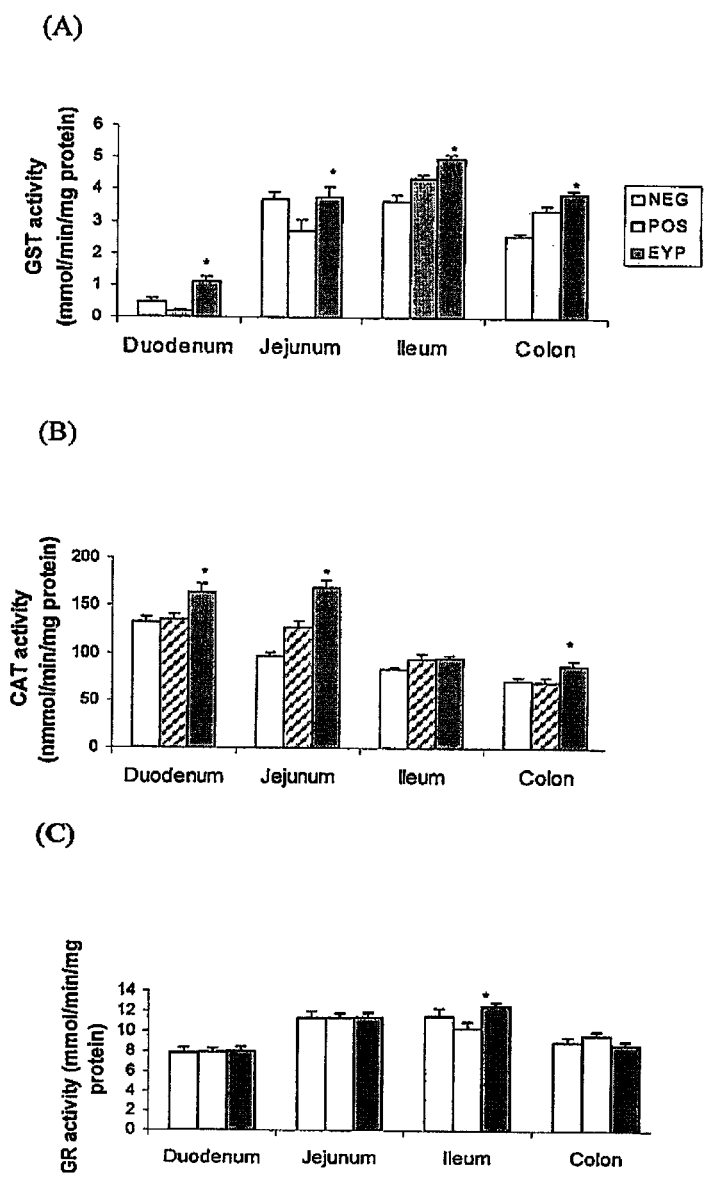
FIGS. 5(A), 5(B) and 5(c) are graphs illustrating GST (glutathione S-transferase, panel A), CAT (catalase, panel B), and GR (glutathione reductase, panel C) activities in intestinal tissues from each of the 3 groups described in FIG. 4 and Example 5. Each bar represents mean+SEM; n=5. $*P<0.05$, compared with positive group.
Figure 6:
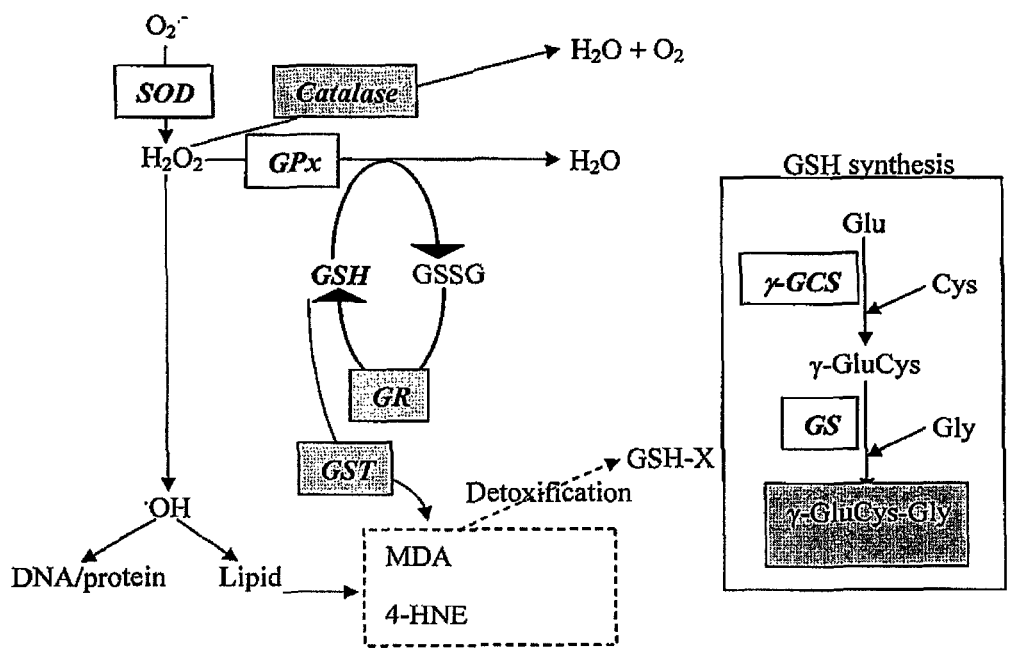
FIG. 6 is a graph illustrating the effects of PPP3 (EY) and EYP on glutathione and antioxidant enzyme activities in vitro and in vivo, respectively.
Figure 6:

With reference to FIG. 5, the Applicant also demonstrated that upon exposing the pigs to $H_2O_2$, the antioxidant enzymes glutathione S-transferase (GST; FIG. 5(A)) and catalase (CAT; FIG. 5(B)) enzymatic activity in intestinal tissues were significantly higher in pigs that were fed with a composition of the present invention comprising EYP prior to the exposure to $H_2O_2$. Antioxidant glutathione reductase (GR) enzymatic activity was also shown to be increased in the ileum in pigs fed with EYP (FIG. 5(c)). Since the glutathione and antioxidant enzyme activity results in the animal trial is quite similar to that obtained in in vitro cell culture the Applicant concluded that PPP3 (EY) is the active component in EYP that has antioxidative properties. This is displayed schematically in FIG. 6.

Figure 7:
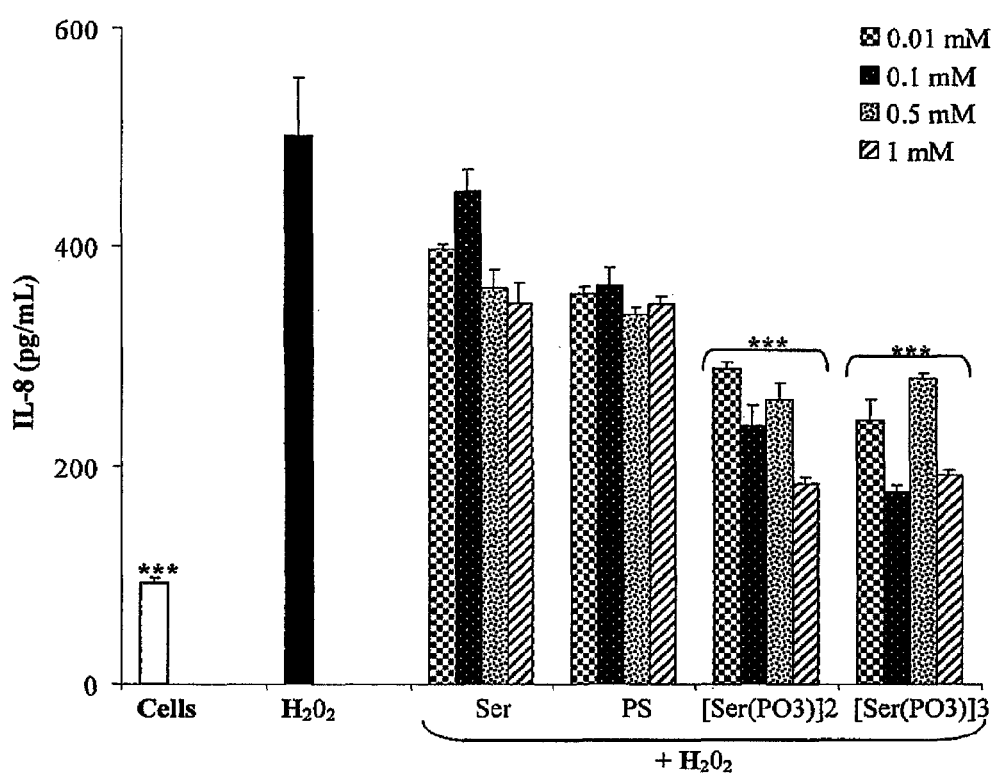
FIG. 7 is a graph illustrating the effect of serine (Ser), phosphoserine (PS), $[Ser(PO_3)]^2$, and $[Ser(PO_3()]^3$, on IL-8 secretion in $H_2O_2$-stimulated Caco-2 cells.

The applicant found that many of the peptides of the invention contained consecutive serine residues, some of which may be phosphorylated. To determine the minimum active portion of the sequence, the applicant treated Caco-2 cells with either serine, phosphoserine, a peptide consisting of 2 consecutive phosphoserine residues $[Ser(PO_3)]^2$ (SEQ ID NO. 15), or a peptide consisting of 3 consecutive phosphoserine residues $[Ser(PO_3)]^3$ (SEQ ID NO. 16) prior to treatment with $H_2O_2$. FIG. 7 illustrates that both $[Ser(PO_3)]^2$ and $[Ser(PO_3)]^3$ inhibited IL-8 secretion in $H_2O_2$ treated Caco-2 cells. These minimum sequences, SEQ ID NO. 15 and 16 are thus capable of inhibiting inflammation and oxidative stress The invention also encompasses therapeutic strategies that involve targeting the oxidative stress signaling pathways to downregulate the production of oxidative stress and pro-inflammatory mediators or disrupting the formation of complexes that stimulate oxidative stress processes. These methods may be used in combination with other known therapies for treating an oxidative stress process.

In humans, oxidative stress is involved in many diseases, such as atherosclerosis, Parkinson's disease, heart failure, myocardial infarction, Alzheimer's disease and chronic fatigue syndrome. As such, the instant invention also encompasses methods for the treatment of oxidative stress related diseases in a subject comprising the administration to the subject of a therapeutic composition comprising one or more of the peptides of the invention and a pharmaceutically acceptable carrier to inhibit the expression and resulting activity of oxidative stress mediators, or to enhance the activity of cellular antioxidants. Examples of cellular antioxidants include, without limitation, glutathione (GSH), superoxidase dismutase (SOD), catalase, thioredoxin reductase, glutathione reductase (GR), glutathione preoxidase, glutathione S-transferase (GST), γ-glutamylcysteine synthetase and glutathione synthetase.

According to another aspect, the present invention relates to a composition for maintaining cells, tissues and/or organs in a viable state ex vivo during storage and in vivo during perfusion, wherein said composition comprises one or more peptides selected from the group comprising of: SEQ ID NOs. 1 to 14 and artificial peptides that include multiple, consecutive serine or phosphoserine residues, such as SEQ ID NOs 15 and 16.

When organs are harvested for transplantation, the ensuing period of hypoxia, followed by reperfusion of the organ, is accompanied by substantial tissue damage, including cell apoptosis and parenchymal dysfunction. Such ischemia/reperfusion (I/R) injury can involve inflammatory reactions that result in the creation of free radicals that further damage the organ.

One or more peptides selected from the group comprising of SEQ ID NOs. 1 to 14 and artificial peptides that include multiple, consecutive serine or phosphoserine residues, such as SEQ ID NOs 15 and 16 can be added to an organ storage or perfusion solution to increase the viability of the cells, tissues and/or organs for transplantation. Storage/perfusion solutions that can be used with the peptides of the invention include any solution for maintaining viability of a cell, tissue or organ. Examples of storage or perfusion solutions include, without limitation, University of Wisconsin (UW) solution (Viaspan®, Dupont Pharma, Wilmington, Del.), Euro-Collins solution and Ringer's solution. The UW solution, is described in U.S. Pat. Nos. 4,798,824 and 4,879,283.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

The examples are described for the purposes of illustration and are not intended to limit the scope of the invention.

Methods of synthetic chemistry, protein and peptide biochemistry, molecular biology, pharmacology and immunology referred to but not explicitly described in this disclosure and examples are reported in the scientific literature and are well known to those skilled in the art.

Example 1

Preparation of Egg Yolk Peptides (EYP)

Egg yolk proteins were partially dephosphorylated using 0.5N NaOH by incubating at 37-50° C. for 2 hours, followed by the addition of two food grade enzymes (microbial alkalase and protease-m). Following appropriate incubations (50° C. for overnight), the enzymes were inactivated by means of heating at 90° C. for 20 min, the proteinaceous mixture centrifuged, and the supernatant was collected and freeze dried for later use.

Example 2

Separation of Bioactive Peptides

Bioactive peptides were isolated using anion-exchange high-performance liquid chromatography (HPLC). Crude phosphopeptides (PPPs-EY) were injected into a Mono-Q HR 5/5 anion exchange column (Pharmacia Biotech, Uppsala, Sweden) and eluted with 20 mM ammonium bicarbonate with a linear NaCl gradient from 0 to 1.0 M. Three fractions were collected, and named PPP-1(EY), PPP-2(EY), and PPP3(EY). Of these three fractions, PPP3 (EY) exhibited the most biological activity and this fraction was analyzed further.

Example 3

Identification of Peptides Amino Acid Sequence

PPP3(EY) was digested by pepsin (at pH 1.5, 37C×2 hours), followed by trypsin digestion (pH 7.5, 37C×8 hours) and subjected to in vitro anti-oxidative activity and peptide mapping.

Peptide amino acid sequence analysis was performed using mass spectrometry. All mass spectra of intact oligopeptides were obtained using matrix-assisted laser ionization/desorption time-of-flight (MALDI-TOF) configuration with a Voyager DE STR spectrometer (Applied Biosystem, Courtaboeuf, France) equipped with a nitrogen laser (337 nm, 20 Hz). All nanoelectrospray mass spectrometry (nES-MS) experiments for peptide mapping were conducted on a Q-TOF hybrid quadrupole/time-of-flight instrument (Micromass, Manchester, UK), for high resolution and on-line liquid chromatography-tandem mass spectrometry (LC-MS/MS) analyses. An external calibration was first performed in the range 500-3000 Da. The monoisotopic mass lists were compared to the Swiss-Prot and TrEMBL protein databanks available on the ExPASy proteomic server (http://us.expasy.org/) using Protein prospector software (http://prospector.ucsf.edu/) for peptide mass fingerprinting (PMF) analysis. The lists of peptide masses were searched against the non-redundant protein sequence database provided by the National Center for Biotechnology Information (NCBI) server (http://www.ncbi.nlm.nih.gov).

Example 4

Antioxidative Activity in Vitro

The antioxidative stress activity of PPP3 (EY) was evaluated in an in vitro cell culture model using the human intestinal epithelial cell line, Caco-2, and hydrogen peroxide. [Katayama S, et al. J. Agric. Food Chem. (2006) 54:773]

Caco-2 cells were treated with digested (dPPP3) and undigested PPP3 (PPP3) for 2 h at 37° C. prior to incubation with 1 mM $H_2O_2$ for 6 h.

FIG. 1 illustrates that pepsin and trypsin-digested dPPP3 (EY) maintained its antioxidative activity as shown by a decrease in IL-8 (FIG. 1). Pepsin and trypsin were used to simulate digestive conditions in the human gut. Upon ingestion of protein/peptides, the stomach's pepsin hydrolyses proteins into large oligopeptides, which then get cleaved into short di- or tripeptides and free amino acids by trypsin, chymotrypsin and aminopeptidases in the small intestine. We hypothesize that owing to PPP3 (EY)'s large size and negative charge, both digested and undigested PPP3 (EY) interact with cell surface receptors and influences intracellular cell signaling in this manner.

Electrophoretic shift mobility assay (EMSA) was used to examine the level of AP-1 and NF-κB transcription factors in the nucleus after pretreatment with PPP3 (EY) and the addition of hydrogen peroxide for 2 hours. Caco-2 cells were pretreated with PPP3 (EY) for 2 h at 37° C. prior to incubation with 1 mM $H_2O_2$ for 30 min. Nuclear extracts were used for EMSA with AP-1 and NF-κB oligonucleotides. EMSA results indicate hydrogen peroxide increases AP-1 and NF-κB DNA binding, however there is a significant reduction of these transcription factors in the presence of PPP3 (EY) (FIG. 2). Reduced AP-1 and NF-KB corresponds to the observed decrease in the pro-inflammatory mediator, IL-8.

Example 5

Antioxidative Activity in Vitro

The in vitro antioxidative activity of egg yolk digests (EYP) was evaluated according to the aforementioned protocol for the antioxidative stress activity of PPP3 (EY). Caco-2 cells were treated with EYP for 2 h at 37° C. prior to incubation with 1 mM $H_2O_2$ for 6 h. The cellular antioxidant and oxidative stress mechanisms are depicted in FIG. 3. Data in FIG. 3 are presented as mean+SD in triplicates. In FIG. 3, IL-8 was significantly reduced in the presence of 0.001-1 mg/mL EYP compared with cells treated with $H_2O_2$ alone (P<0.05). This is particularly interesting since EYP is reducing IL-8 concentrations similar to that observed with PPP3 (EY), which indicates that the active component in EYP is likely PPP3 (EY).

Example 6

Antioxidative Activity in Vivo

Experimental Animals

Fifteen male and female 3-5 day old Yorkshire piglets were obtained from the University of Guelph Arkell Swine Research Station and then housed individually in a temperature controlled room (average 25° C.) with a 14-hour fight-dark cycle beginning at 600 h. Piglets were given a day's adaptation to a commercial liquid formula (Soweena® Litter Life-Merrick's Inc. Wis.) prior to undergoing surgery for the placement of intraperitoneal (i.p.) catheters. After 3 days' recovery, the piglets were randomly assigned to 3 groups of 5 animals each. All experiments were approved by the Animal Care Committee (University of Guelph, Canada), and animals were cared for in compliance with the guidelines established by the Canadian Council of Animal Care.

In Vivo Induction of Oxidative Stress

Regardless of group assignment, piglets were fed close to their ad libitum intake three times per day, and food intake and piglets weights were monitored daily. The 3 experimental groups consisted of negative controls (NEG), positive controls (POS), and egg yolk peptide (EYP). For ten consecutive days, both POS and EYP groups were i.p. infused with a low dose of hydrogen peroxide/kg body weight/day which was dissolved in sterile saline. NEG groups were infused with sterile saline only. At the same time EYP piglets were fed 250 mg crude protein of EYP; and NEG and POS groups were fed an equivalent amount of alanine (Sigma-Aldrich, Saint Louis, Mo.) to balance the nitrogen content contributed by the EYP. On the day following the treatment course, piglets were sacrificed and intestinal tissues were harvested and frozen in liquid nitrogen for future measurement of biochemical parameters. Blood samples were taken throughout the course of the trial on days 8, 11, 14 and 17 and placed in potassium EDTA blood tubes (BD Vacutainer, Franklin Lakes, N.J.). Whole blood was centrifuged (2500 rpm, 20 min, 25° C.), followed by plasma and red blood cell separation and preparation for GSH analysis.

Total GSH Analysis of Red Blood Cells (RBC)

A 4× volume of ice cold MilliQ water was mixed with the red blood cells, centrifuged, and the supernatant removed. An equal volume of 10% metaphosphoric acid (MPA) was added to the lysed cells, centrifuged and the supernatant removed. The RBC-MPA supernatant was neutralized with triethanolamine prior to use in the assay. The supernatant was mixed with 100 mM PBS containing 4 mM EDTA, 0.2 mM NADPH, and 0.5 mM DTNB and 100 units/mL GR. The mixture was incubated for 5 min at 25° C., and the absorbance was measured at 412 nm. The concentration of GSH in the red blood cells was calculated using a standard curve and expressed as micromoles of GSH per gram of protein.

As shown in FIG. 4, on days 11, 14 and 17, total GSH levels in EYP pigs were significantly higher compared to both NEG and POS pigs (P<0.05). This indicates that EYP is able to influence the production of GSH and may do so via γ-GCS. Further mRNA expression and enzyme activity assays will be conducted to confirm this.

Measurement of GST, CAT, and GR Activity in Intestinal Tissues

Intestinal tissues from each of the 3 groups of pigs were excised upon sacrifice of the animals (day 18), and were homogenized in a 100 mM potassium phosphate buffer with 1 mM EDTA. The intestinal tissue samples were centrifuged (10,000 g, 15 min, 4° C.) and the supernatant was collected for the antioxidant enzyme assays. GST, CAT, and GR activity was measured according to the protocols noted by Katayama et al. (2007). [J. Agric. Food Chem. (2007) 55:2829]

In FIGS. 5(A) and 5(B) both GST and CAT enzyme activities were significantly higher for EYP versus POS control intestinal tissues with the exception of CAT activity in the ileum. GR activity was only significantly higher in EYP compared to POS tissues in the ileum (FIG. 5(C)). P<0.05.

The glutathione and antioxidant enzyme activity results in the animal trial is quite similar to that that obtained in in vitro cell culture, thus indicating that PPP3 (EY) is the active component in EYP that has antioxidative stress properties. This is displayed schematically in FIG. 6.

Statistical Analysis

In vivo biomarker results are expressed as mean+SEM. Statistical analyses were carried out using the GraphPad Software (San Diego, Calif.). Comparisons between groups were calculated with one-way analysis of variance (ANOVA) followed by Tukey-Kramer multiple comparison test. A probability of less than 0.05 was considered statistically significant.

Example 7

Effect of Serine and Phosphoserine on IL-8 Secretion

FIG. 7 is a graph illustrating the effect of serine (Ser), phosphoserine (PS), [Ser(PO3)]2, and [Ser(PO3)]3, on IL-8 secretion in $H_2O_2$-stimulated Caco-2 cells. Cells were cultured with 5% FBS-DMEM/F12 and treated with 0.01, 0.1, 0.5, or 1.0 mM of Ser, PS, $[Ser(PO_3)]^2$, or $[Ser(PO_3)]^3$ for 2 h at 37° C., and then incubated with 1 mM $H_2O_2$ for 6 h. Data in FIG. 7 are presented as mean+SEM in three wells. ***P<0.001 compared to $H_2O_2$-treated cells.

Example 8

Identification of Active Phosphopeptide Sequences

Table 1 (Sequence Listing) provides the results of peptide sequence mapping. There are two major sequences in the active peptides. It is likely the core and key sequences of biological activities are sequences comprising continuous phosphoserine residues (2 or more), or sequences comprising one or more clusters of at least 2 phosphoserines residues within the peptide sequence.

Example 9

Isolated Peptides

One or more of the peptides identified in fraction PPP3 (EY) and in fraction dPPP3 (Y) (SEQ ID NOs. 1 to 14) can be synthesized by any known method of peptide synthesis and evaluated for their antioxidant potential using any of the experiments described above in Examples 4 to 7 or by other assays, such as the ORAC (Oxygen Radical Absorbance Capacity assay). The ORAC assay measures the scavenging capacity of antioxidant nutrients against the peroxyl radical [Diehl-Jones W L and Askin D F. American Association of Critical Care Nurses (AACN) Clin Issues 15: 83 (2004)], which is one of the most common reactive oxygen species (ROS) in the human body.

Example 10

Organ Storage Solution

An organ for transplantation is removed from a donor and stored in cold (4° C.) ViaSpan™ solution containing one or more peptides of the invention capable of inducing an antioxidative response. The organ is carried to the OR immersed in the ViaSpan™ composition containing the peptides of the invention capable of inducing an antioxidative response and kept in the solution until transplantation.

The invention claimed is:
1. A method for the treatment of an oxidative stress related disorder in a subject, characterized in that said method comprises administering an effective amount of a pharmaceutical composition to said subject, said pharmaceutical composition comprising an artificial dipeptide of SEQ ID NO:15, and a pharmaceutically acceptable carrier.

* * * * *

SEQUENCE LISTING

```
<160> NUMBER OF SEQ ID NOS: 17

<210> SEQ ID NO 1
<211> LENGTH: 38
<212> TYPE: PRT
<213> ORGANISM: Gallus domesticus
```

```
<400> SEQUENCE: 1

Gly Thr Glu Pro Asp Ala Lys Thr Ser Ser Ser Ser Ser Ala Ser
1               5                   10                  15

Ser Thr Ala Thr Ser Ser Ser Ser Ser Ala Ser Ser Pro Asn Arg
            20                  25                  30

Lys Lys Pro Met Asp Glu
        35

<210> SEQ ID NO 2
<211> LENGTH: 19
<212> TYPE: PRT
<213> ORGANISM: Gallus domesticus

<400> SEQUENCE: 2

Glu Asp Asp Ser Ser Ser Ser Ser Ser Ser Val Leu Ser Lys Ile
1               5                   10                  15

Trp Gly Arg

<210> SEQ ID NO 3
<211> LENGTH: 37
<212> TYPE: PRT
<213> ORGANISM: Gallus domesticus

<400> SEQUENCE: 3

Gly Thr Glu Pro Asp Ala Lys Thr Ser Ser Ser Ser Ser Ala Ser
1               5                   10                  15

Ser Thr Ala Thr Ser Ser Ser Ser Ser Ala Ser Ser Pro Asn Arg
            20                  25                  30

Lys Lys Pro Met Asp
        35

<210> SEQ ID NO 4
<211> LENGTH: 31
<212> TYPE: PRT
<213> ORGANISM: Gallus domesticus

<400> SEQUENCE: 4

Gly Thr Glu Pro Asp Ala Lys Thr Ser Ser Ser Ser Ser Ala Ser
1               5                   10                  15

Ser Thr Ala Thr Ser Ser Ser Ser Ser Ala Ser Ser Pro Asn
            20                  25                  30

<210> SEQ ID NO 5
<211> LENGTH: 32
<212> TYPE: PRT
<213> ORGANISM: Gallus domesticus

<400> SEQUENCE: 5

Gly Thr Glu Pro Asp Ala Lys Thr Ser Ser Ser Ser Ser Ala Ser
1               5                   10                  15

Ser Thr Ala Thr Ser Ser Ser Ser Ser Ala Ser Ser Pro Asn Arg
            20                  25                  30

<210> SEQ ID NO 6
<211> LENGTH: 25
<212> TYPE: PRT
<213> ORGANISM: Gallus domesticus

<400> SEQUENCE: 6

Thr Ser Ser Ser Ser Ser Ser Ala Ser Ser Thr Ala Thr Ser Ser Ser
1               5                   10                  15
```

-continued

Ser Ser Ser Ala Ser Ser Pro Asn Arg
            20              25

<210> SEQ ID NO 7
<211> LENGTH: 13
<212> TYPE: PRT
<213> ORGANISM: Gallus domesticus

<400> SEQUENCE: 7

Ser Ser Ser Ala Ser Ser Thr Ala Thr Ser Ser Ser Ser
1               5                   10

<210> SEQ ID NO 8
<211> LENGTH: 5
<212> TYPE: PRT
<213> ORGANISM: Gallus domesticus

<400> SEQUENCE: 8

Ser Ala Ser Ser Thr
1               5

<210> SEQ ID NO 9
<211> LENGTH: 15
<212> TYPE: PRT
<213> ORGANISM: Gallus domesticus

<400> SEQUENCE: 9

Glu Asp Asp Ser Ser Ser Ser Ser Ser Ser Val Leu Ser Lys
1               5                   10                  15

<210> SEQ ID NO 10
<211> LENGTH: 12
<212> TYPE: PRT
<213> ORGANISM: Gallus domesticus

<400> SEQUENCE: 10

Asp Asp Ser Ser Ser Ser Ser Ser Ser Val Leu
1               5                   10

<210> SEQ ID NO 11
<211> LENGTH: 14
<212> TYPE: PRT
<213> ORGANISM: Gallus domesticus

<400> SEQUENCE: 11

Asp Asp Ser Ser Ser Ser Ser Ser Ser Val Leu Ser Lys
1               5                   10

<210> SEQ ID NO 12
<211> LENGTH: 15
<212> TYPE: PRT
<213> ORGANISM: Gallus domesticus

<400> SEQUENCE: 12

Asp Asp Ser Ser Ser Ser Ser Ser Ser Val Leu Ser Lys Ile
1               5                   10                  15

<210> SEQ ID NO 13
<211> LENGTH: 16
<212> TYPE: PRT
<213> ORGANISM: Gallus domesticus

<400> SEQUENCE: 13

Asp Asp Ser Ser Ser Ser Ser Ser Ser Val Leu Ser Lys Ile Trp
1               5                   10                  15

```
<210> SEQ ID NO 14
<211> LENGTH: 17
<212> TYPE: PRT
<213> ORGANISM: Gallus domesticus

<400> SEQUENCE: 14

Asp Asp Ser Ser Ser Ser Ser Ser Ser Val Leu Ser Lys Ile Trp
1               5                   10                  15

Gly

<210> SEQ ID NO 15
<211> LENGTH: 2
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(2)
<223> OTHER INFORMATION: Phosphoserine

<400> SEQUENCE: 15

Xaa Xaa
1

<210> SEQ ID NO 16
<211> LENGTH: 3
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(3)
<223> OTHER INFORMATION: Phosphoserine

<400> SEQUENCE: 16

Xaa Xaa Xaa
1

<210> SEQ ID NO 17
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa, if present, is T (Threonine), D (Aspartic
      acid), A (Alanine), P (Proline), V (Valine), K (Lysine), E
      (Glutamic Acid) or I (Isoleucine)
<220> FEATURE:
<221> NAME/KEY: misc_feature
<222> LOCATION: (2)..(3)
<223> OTHER INFORMATION: Xaa is Serine or Phosphoserine
<220> FEATURE:
<221> NAME/KEY: misc_feature
<222> LOCATION: (2)..(3)
<223> OTHER INFORMATION: Xaa may repeat indefinitely
<220> FEATURE:
<221> NAME/KEY: misc_feature
<222> LOCATION: (4)..(4)
<223> OTHER INFORMATION: Xaa, if present, is T (Threonine), D (Aspartic
      acid), A (Alanine), P (Proline), V (Valine), K (Lysine), E
      (Glutamic Acid) or I (Isoleucine)

<400> SEQUENCE: 17

Xaa Xaa Xaa Xaa
1
```